United States Patent [19]

James et al.

[11] Patent Number: 5,480,450
[45] Date of Patent: Jan. 2, 1996

[54] METHOD AND APPARATUS FOR REDUCING INTERFACIAL POROSITY IN A CEMENTED FEMORAL PROSTHESIS

[75] Inventors: Susan P. James, Boston; Daphne Karydas, Sharon; Frederick M. McGarry, Weston; William H. Harris, Belmont, all of Mass.

[73] Assignees: The General Hospital Corporation, Boston; Massachusetts Institute of Technology, Cambridge, both of Mass.

[21] Appl. No.: 16,697

[22] Filed: Feb. 11, 1993

[51] Int. Cl.$^6$ .................................................. A61F 2/36
[52] U.S. Cl. .................................. 623/23; 623/18; 606/92
[58] Field of Search ................ 623/16, 23; 606/92–95

[56] References Cited

U.S. PATENT DOCUMENTS

| | | |
|---|---|---|
| 2,682,265 | 6/1954 | Collison . |
| 2,719,522 | 10/1955 | Hudack . |
| 3,829,904 | 8/1974 | Ling et al. . |
| 4,012,796 | 3/1977 | Weisman et al. . |
| 4,068,324 | 1/1978 | Townley et al. . |
| 4,222,382 | 9/1980 | Antonsson et al. ............ 623/23 X |
| 4,276,659 | 7/1981 | Hardinge . |
| 4,312,079 | 1/1982 | Dörre et al. ........................ 623/23 |
| 4,357,716 | 11/1982 | Brown ............................... 606/94 |
| 4,385,405 | 5/1983 | Teinturier ........................ 623/23 X |
| 4,399,814 | 8/1983 | Pratt, Jr. et al. ................. 606/94 |
| 4,488,549 | 12/1984 | Lee et al. ........................ 606/94 |
| 4,535,487 | 8/1985 | Esper et al. . |
| 4,593,685 | 6/1986 | McKay et al. ................ 606/92 X |
| 4,623,353 | 11/1986 | Buechel et al. . |
| 4,625,722 | 12/1986 | Murray ............................ 606/94 |
| 4,678,471 | 7/1987 | Noble et al. . |
| 4,745,914 | 5/1988 | Frey et al. . |
| 4,770,660 | 9/1988 | Averill . |
| 4,783,192 | 11/1988 | Wroblewski et al. . |
| 4,790,852 | 12/1988 | Noiles ............................. 623/23 X |
| 4,815,454 | 3/1989 | Dozier, Jr. ....................... 606/94 |
| 4,881,536 | 11/1989 | Noble et al. .................... 606/94 |
| 4,896,662 | 1/1990 | Noble ........................... 606/92 X |
| 4,908,036 | 3/1990 | Link et al. ....................... 623/23 |

(List continued on next page.)

FOREIGN PATENT DOCUMENTS

| | | |
|---|---|---|
| 6408 | 1/1980 | European Pat. Off. . |
| 0022308 | 1/1981 | European Pat. Off. ............... 606/92 |
| 220427 | 9/1986 | European Pat. Off. . |
| 1409053 | 10/1975 | United Kingdom . |
| 2052267 | 1/1981 | United Kingdom . |
| 2104391 | 3/1983 | United Kingdom . |

OTHER PUBLICATIONS

S. P. James, T. P. Schmalzried, F. J. McGarry and W. H. Harris, "Extensive porosity at the cement-femoral prosthesis interface: A preliminary study", Journal of Biomedical Materials Research, vol. 27, 71–78 (1993).

Primary Examiner—David Isabella
Assistant Examiner—Laura Fossum
Attorney, Agent, or Firm—Wolf, Greenfield & Sacks

[57] ABSTRACT

A diaphragm for minimizing interfacial porosity during the insertion of a femoral component into the cavity in the medullary canal of a femur. By providing a seal around the outer medial, lateral, anterior and posterior surfaces of the component during insertion through the diaphragm, the introduction of pores into the cement during the insertion process is minimized and flow of cement out of the cavity is resisted. The diaphragm may be formed of at least one rigid layer and a resilient layer, the resilient layer providing the desired seal. In another embodiment, the diaphragm may be formed of two stacked discs which permit expansion in two orthogonal directions and which have holes which include seals on the inner surface thereof to provide a seal between the diaphragm and the outer surfaces of the component. In the method of the present invention, a diaphragm is placed over the opening of the cavity to resist the flow of cement out of the cavity to pressurize the cement during insertion of the component, as well as to provide a seal between the diaphragm and the component to resist the introduction of air into the cement. After insertion, the diaphragm is cut or otherwise separated to allow removal thereof.

18 Claims, 6 Drawing Sheets

U.S. PATENT DOCUMENTS

| | | | |
|---|---|---|---|
| 4,936,863 | 6/1990 | Hofmann . | |
| 4,946,379 | 8/1990 | Berchem . | |
| 4,978,357 | 12/1990 | Goymann et al. | 623/23 X |
| 4,997,448 | 3/1991 | Filer | 606/92 X |
| 5,009,666 | 4/1991 | Van Syckle et al. | 623/23 |
| 5,037,425 | 8/1991 | Brown | 606/92 |
| 5,047,061 | 9/1991 | Brown | 606/92 X |
| 5,092,892 | 3/1992 | Ashby . | |
| 5,108,452 | 4/1992 | Fallin . | |
| 5,116,380 | 5/1992 | Hewka et al. | 623/23 |
| 5,147,366 | 9/1992 | Arroyo et al. | 606/92 X |

METHOD AND APPARATUS FOR REDUCING INTERFACIAL POROSITY IN A CEMENTED FEMORAL PROSTHESIS

FIELD OF THE INVENTION

This invention relates generally to prostheses, and more particularly to a method and apparatus for reducing the porosity in the cement at the cement-metal interface of the femoral component of an artificial human hip prosthesis.

BACKGROUND OF THE INVENTION

Load-carrying skeletal members, such as a human hip, frequently are rendered non-functional because of fracture, damage, disease, resections for malignancy or disease, or because of pain or malformation. Such members are commonly repaired by total joint replacements with artificial components. One type of bone replacement that has been particularly successful over the past thirty years is that of the human hip. Such hip prostheses typically include a femoral portion or component which is implanted in the femur and an acetabular component which is secured to the pelvis. The femoral component includes a head which rotates in a socket formed in the acetabular component. The femoral component typically has a rectangular or square cross-sectional shape and includes four outer surfaces, the lateral, medial, anterior and posterior surfaces.

Many known hip prostheses require the use of cement for installation of the femoral component into the medullary canal of the femur. One type of cement which is commonly used is a polymethylmethacrylate.

Success of a femoral component of a total hip implant depends in large part On the technical precision with which the implant is inserted. One factor which contributes to the success of a femoral component is centering of the component within the central cavity in the medullary canal of the femur into which the component is inserted. Centering of the component insures that the thickness of the cement mantle surrounding the component is uniform on all sides. Uniformity of the cement mantle renders the load distribution at the bone-cement and metal-cement interfaces generally uniform on all sides of the component, thus avoiding problems associated with overstressing one area of the interface, such as fracturing of the mantle, separation of the mantle from the bone or separation of the component from the mantle. Another factor which has been identified as contributing to the success of either an uncemented or cemented component is proper rotational position of the femoral component about its axis with respect to the femur. Proper rotational position, or anteversion, allows for accurate reproduction of the mechanical orientation of hip joints and produces the desired stability and range of motion.

A third factor believed to contribute to the success of a cemented femoral component is the bond between the cement and the inner surfaces of the cavity in the medullary canal of the femur. This bond can be improved by distributing the cement into the trabecular bone. To achieve such a result, it is a common practice to pressurize the cement prior to insertion of the femoral component.

A fourth factor which recently has been recognized to be crucial to the long term stability of cemented femoral components in total hip replacements is the strength of the bond between the bone cement and metal of the femoral component. The interface between the prosthesis and bone cement has been determined to be the weak link in the mechanical integrity of the femoral component. Conversely, a secure cement-metal interface provides an even load distribution with respect to the surrounding cement, and thus decreases localized loading and reduces the risk of cement fracture. It has been established that debonding of the cement-metal interface is the initiating event in the failure of fixation of cemented femoral components. Fractures in the cement mantle are usually associated with debonding at the cement-metal interface, and radial cement fractures propogate from the cement-metal interface outwardly. Moreover, it has been found that debonding of the cement-metal interface starts in the proximal and distal regions of the mantle and progresses toward the middle of the component.

Recent studies have shown that abundant porosity in the cement at the cement-metal interface is one cause of debonding. In many failed femoral prostheses, there existed a high concentration of pores in the cement at the cement-metal interface relative to the concentration of pores in the bulk cement mantle. This porosity will hereinafter be referred to as "interfacial porosity". In experiments it was observed that interfacial pores formed because air was pulled down along the interface between the metal and the cement. If the cement had had a lower viscosity, it would have fully contacted the surface of the metal and filled in the areas left by displaced air. However, the cement was too viscous to do so. During curing, the pores at the interface expanded as the cement started to heat, and then after the peak temperature is reached, the pores puckered. This heating caused new pores to appear at the interface. These pores were formerly located only a few microns away from the interface and expanded to reach the interface. Such interfacial porosity was not observed to be affected by the type of prostheses, surface finish or by cement centrifugation. Interfacial porosity is believed to be detrimental to the long-term mechanical integrity of the femoral component because it reduces the effective surface area for cement-metal bonding and causes stress concentrations in the cement which may initiate cracks.

This interfacial porosity was determined to be a result of the rheology of the cement during the insertion of the implant (S. P. James, T. P. Schmalzried, F. J. McGarry and W. H. Harris, "Extensive Porosity at the Cement-Femoral Prosthesis Interface: A Preliminary Study", 27 J. Biomed. Mater. Res., 71 (1993)). The observed porosity was aligned with stem geometry and in some specimens was concentrated in the highest stress areas: the proximal and distal portions of the interface. This combination of high stress and extensive porosity is believed to explain why debonding starts in the proximal and distal regions.

It is therefore an object of the present invention to provide a method and apparatus for reducing interfacial porosity in the cement at the cement-metal interface of a femoral component.

It is another object of the present invention to provide a method and apparatus for reducing the porosity in the cement at the metal-cement interface of a femoral component which can be utilized in conjunction with existing prostheses.

It is a further object of the present invention to provide apparatus for reducing the porosity in the cement at the metal-cement interface of a femoral component which can be removed after use without disturbing the position and angular orientation of the component.

It is another further object of the present invention to provide a method and apparatus for centering a femoral component during implantation into a femur.

It is yet another further object of the present invention to provide a method and apparatus for controlling the angular position of the femoral component during insertion thereof into a femur.

SUMMARY OF THE INVENTION

These and other objects of the invention are achieved by a method and apparatus which includes a removable, disposable diaphragm placed over the proximal opening of the cavity in the femoral medullary canal, after the cavity has been prepared for insertion of the femoral component. This diaphragm typically is held in place by the hand of the surgeon during insertion of the femoral component. The diaphragm includes a hole positioned in the appropriate location through which the component is inserted, and sealing means to provide a relatively airtight seal between the lateral, medial, anterior and posterior surfaces of the femoral component and the diaphragm to prevent air from being drawn into the cement during insertion of the component, and to prevent the escape of cement immediately adjacent the outer surfaces of the femoral component.

The diaphragm is sufficiently rigid to resist the cement pressure within the cavity and to direct the flow of the cement exiting the cavity during insertion so that the cement exits only at the outer edges of the diaphragm. Also, the diaphragm is sufficiently resilient and deformable at the interface between the diaphragm and the outer surfaces of the component to provide the desired seal. The diaphragm also is capable of being removed from the proximal end of the femur without disturbing the lateral and angular position of the femoral component. Finally, the diaphragm preferably is formed of a material free of contaminants.

In one embodiment, the diaphragm comprises a layer of a relatively rigid material, such as a plastic, and a less rigid layer of a relatively resilient material, such as an elastomeric foam, bonded to one side of the rigid layer. Both the resilient layer and the rigid layer are provided with an opening through which the component can be inserted. The opening in the resilient layer is configured to have the same general cross-sectional shape as the femoral component but is no larger in cross section than the cross-sectional size of the tip of the femoral component. The opening in the rigid layer can have any shape but its cross-sectional size is at least as large as the largest cross-sectional dimension of the femoral component. The opening in the rigid layer must extend to one edge thereof to allow one to slice through the resilient layer for lateral removal of the diaphragm. In another embodiment, a layer of relatively resilient material, such as an elastomeric foam is positioned between two layers of relatively rigid material, such as a plastic. In this embodiment, both rigid layers have openings extending to an edge with approximately the same cross-sectional size and shape as described above, while the intermediate resilient layer has a smaller size hole as previously described for the resilient layer of the first embodiment. In a third embodiment, a single, relatively rigid layer of a resilient material, such as a foam, is provided having an opening with the size described above for the resilient layer of the first embodiment.

A fourth embodiment includes two stacked, relatively rigid discs, one above the other. Each rigid disc is comprised of two segments. Each pair of segments has a hole formed by cutouts along the abutting edges at which they meet. Each pair of segments is held together along their abutting edges by an elastic or spring material which biases together the abutting edges of the segments. The abutting edges of one disc are aligned generally perpendicularly with respect to the abutting edges of the other disc so that each pair of segments of one disc is permitted to expand apart in a direction generally normal to the direction of expansion of the other pair of segments of the other disc. Each hole in each disc is provided with a seal for providing a relatively airtight seal between the component and the diaphragm.

In the method of this invention, the diaphragm is placed over the opening of the cavity in the medullary canal at the proximal end of the femur. The diaphragm is held in place by one hand of the surgeon. The surgeon then inserts the femoral component through a hole in the central part of the diaphragm while holding the diaphragm firmly in place. This diaphragm controls the exit of the cement from the cavity, keeps out air and changes the flow patterns of the cement, so that there is a firm and pore-free interface between the cement and the component.

The diaphragm is removed once the collar of the component comes into contact with the diaphragm. In the embodiment utilizing a resilient layer and one or two rigid layers, the diaphragm is removed by cutting the resilient layer on the medial side of the component from an edge to the hole and sliding the diaphragm laterally through the slot in the rigid layer. If a single resilient layer is used, it also can be cut and slid off. In the fourth embodiment, the diaphragm is removed by either cutting or removing the elastic bands or springs holding the segments together to permit separation thereof and lateral removal from the prosthesis.

The diaphragm of this invention also can be used for centering of the component and for aligning the component with the desired angular position by properly adjusting the position of the diaphragm adjacent the opening of the cavity at the proximal end of the femur. Moreover, since the diaphragm of this invention pressurizes the cement in the cavity, it assists in the distribution of the cement into the trabecular bone and permits elimination of the conventional pressurization step prior to insertion of the component.

DESCRIPTION OF THE DRAWINGS

The invention will be more fully appreciated from the following detailed description when taken in conjunction with the accompanying drawings, in which.

DESCRIPTION OF THE PREFERRED EMBODIMENTS

Figure 1:
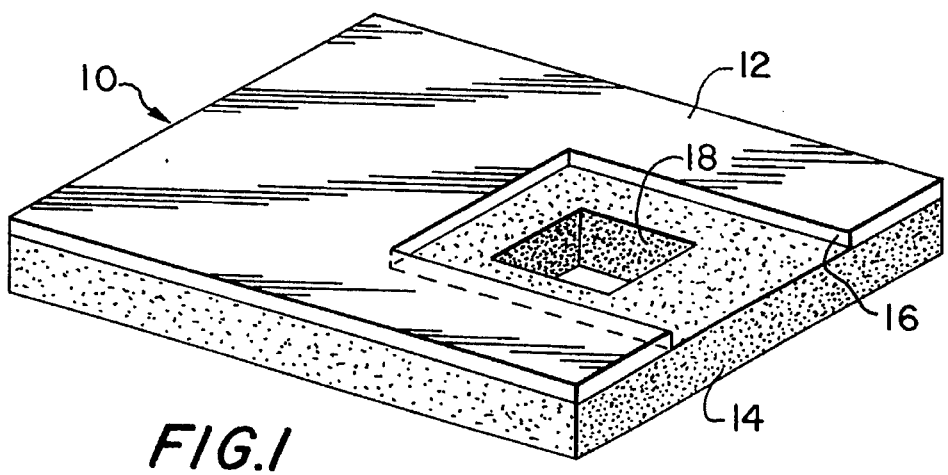
FIG. 1 is a perspective view of a first embodiment of the diaphragm of the present invention.

The porosity observed on the interface between a metal femoral component and the cement can be minimized if not substantially eliminated altogether by significantly reducing the amount of air drawn into the cement during insertion of the femoral component and also by restricting the flow of the displaced bone cement out of the cavity and urging it into contact with the surface of the component as the component is inserted into the cement-filled cavity in the proximal femur. These two functions are performed by a diaphragm which both covers completely the opening of the cavity formed in the proximal end of the femur and provides a seal around the anterior, posterior, medial and lateral surfaces of the component as it is being inserted into the opening of the cavity. The diaphragm of the present invention also is easily removable once the component is inserted without altering the location or rotational position of the component within the femur.

One embodiment of a diaphragm which performs the foregoing functions will now be described with reference to the drawings, and more particularly, to FIGS. 1 and 2 thereof. Diaphragm 10 comprises a relatively rigid support layer 12 and a relatively flexible, resilient layer 14. Layer 12 includes a slot 16, while layer 14 includes a hole 18. Hole 18 is disposed within slot 16, typically at one end thereof. Slot 16 has an open end along one edge of diaphragm 10. Hole 18 may be roughly centered or it may be off-center, as shown in FIG. 1, disposed closer to an edge adjacent the open end of slot 16 than to an edge facing the closed end of slot 16 in layer 14.

Figure 5:
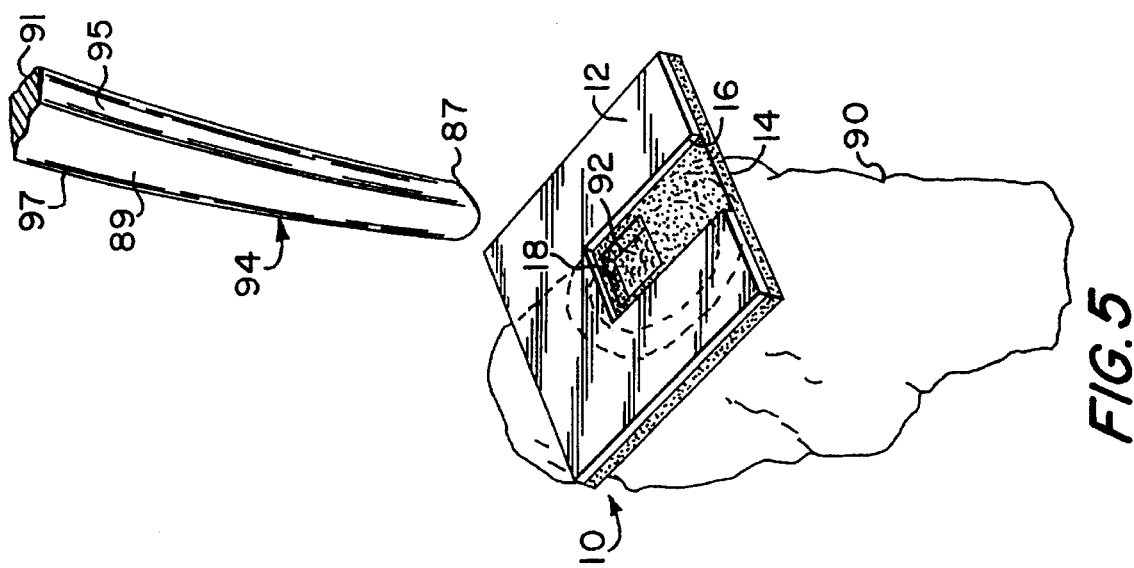

Layer 12 provides the necessary rigidity for directing the flow of the cement as it is being displaced out of the femoral cavity, while layer 14 has sufficient flexibility or elasticity to allow hole 18 to expand as the component passes therethrough, while maintaining a tight seal between layer 14 and the anterior 89, posterior 91, lateral 97 and medial 95 surfaces of the component (FIG. 5). Typically, hole 18 has a cross sectional size and shape which conforms to that of the tip of a conventional femoral component. As the tip of the component is inserted into hole 18, and as its cross-section expands and changes, hole 18 expands to accommodate this change, maintaining a tight seal between the resilient material of layer 14, and the outer surfaces of the component. Layer 14 must also be sufficiently thin that it can be easily severed in the vicinity of slot 16 to provide an avenue in layer 14 from hole 18 to the open end of slot 16 to permit lateral removal of diaphragm 10 after insertion of the prosthesis, as will be more fully described.

Figure 2:
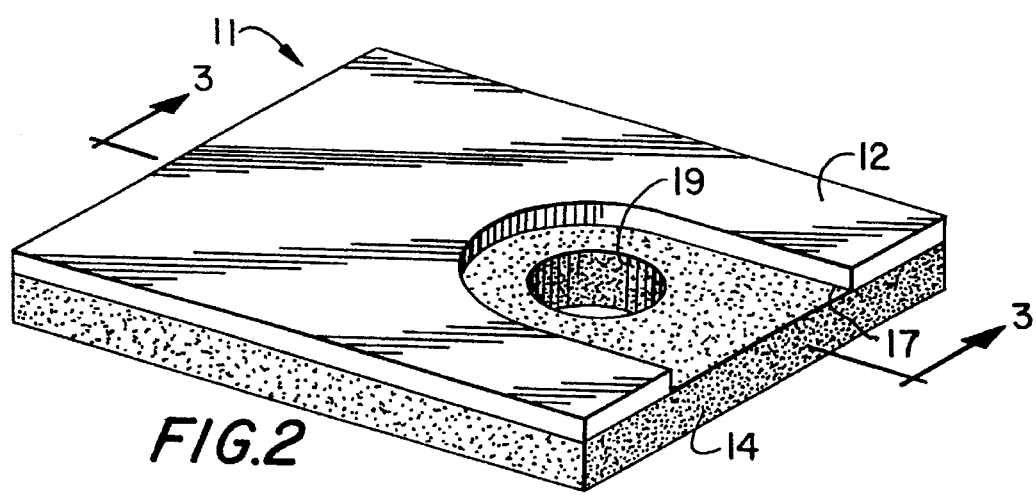
FIG. 2 is a perspective view of an alternative of the embodiment FIG. 1.

FIG. 2 illustrates diaphragm 11, a variation of the embodiment of FIG. 1, and like numbers are used for like parts. In diaphragm 11, hole 19 is circular, and slot 17 has an eliptical or semi-circular shape. In all other respectives, the diaphragm 11 of FIG. 2 is the same as diaphragm 10 of FIG. 1.

Layer 14 must be flexible, resilient and have good tear resistance. Layer 14 is typically less dense than layer 12. Layer 14 could be formed of any one of a number of flexible foams including either an open cell or closed cell foam. Suitable foams could be made of any number of cross-linked elastomers such as polyurethanes (polyether or polyester based), polyethylenes, silicone rubbers, fluoropolymers or the like. In an alternative embodiment, layer 14 could be formed of a cross-linked elastomer instead of a foam. Several suitable cross-linked elastomers include nitrile rubbers (polyacronitrile-butadiene copolymer), neoprene (polychloroprene), butyl rubbers (polyisobutylene-isoprene copolymer), and silicone rubbers. Moreover, layer 14 must be clean, and must not coat the surfaces of the component with any substance during the insertion process. Examples of unacceptable contaminants are surfactants, such as silicone, chemical blowing agents, low molecular weight stabilizers or other moieties which do not fully react, mold-release agents and plasticizers. Such contaminants would be acceptable, if the foam or elastomer was cross-linked, since these contaminants could be removed after processing by cleaning with the proper solvent.

Layer 12 is formed of any rigid or semi-rigid material, such as a plastic or a metallic alloy. Suitable plastics would include polymethylmethacrylate, polycarbonate, polystyrene or the like. A suitable metallic alloy would be aluminum.

Another embodiment of the diaphragm of this invention will now be described with reference to FIG. 3. Diaphragm 20 includes relatively rigid layers 22 and 24 and a resilient layer 26 sandwiched therebetween. Rigid layers 22 and 24 are both provided with substantially identical slots 28, while layer 26 is provided with hole 30. Diaphragm 20 is identical to either diaphragm 10 or 11 except for the provision of a rigid layer on each opposite side of the resilient layer.

Figure 3:
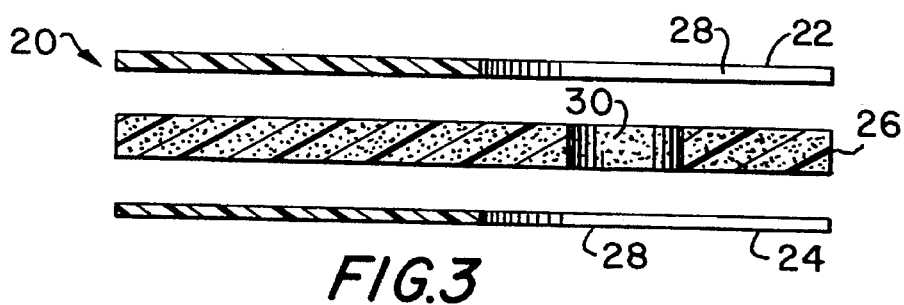
FIG. 3 is an exploded side, cross-sectional view of a second embodiment of the diaphragm of the present invention.
Figure 7:
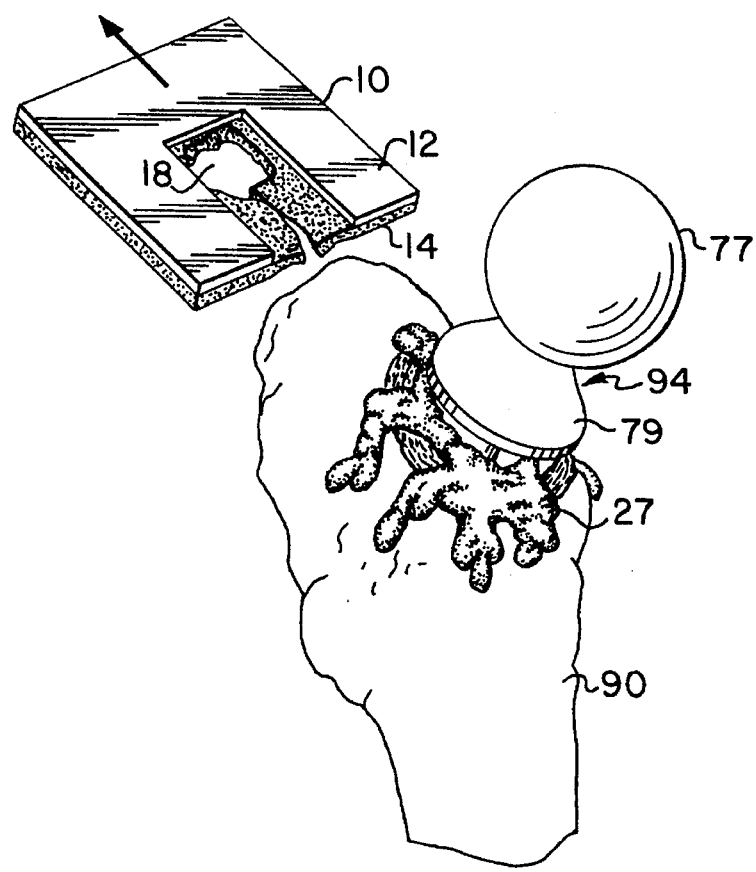
Figure 8:
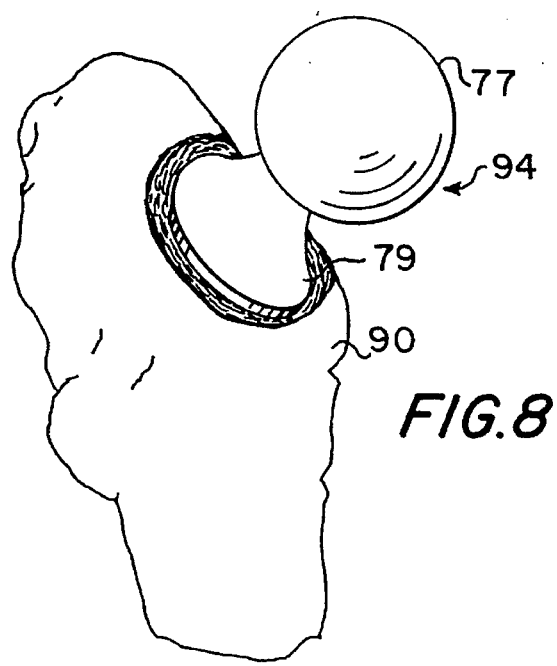
Figure 9:
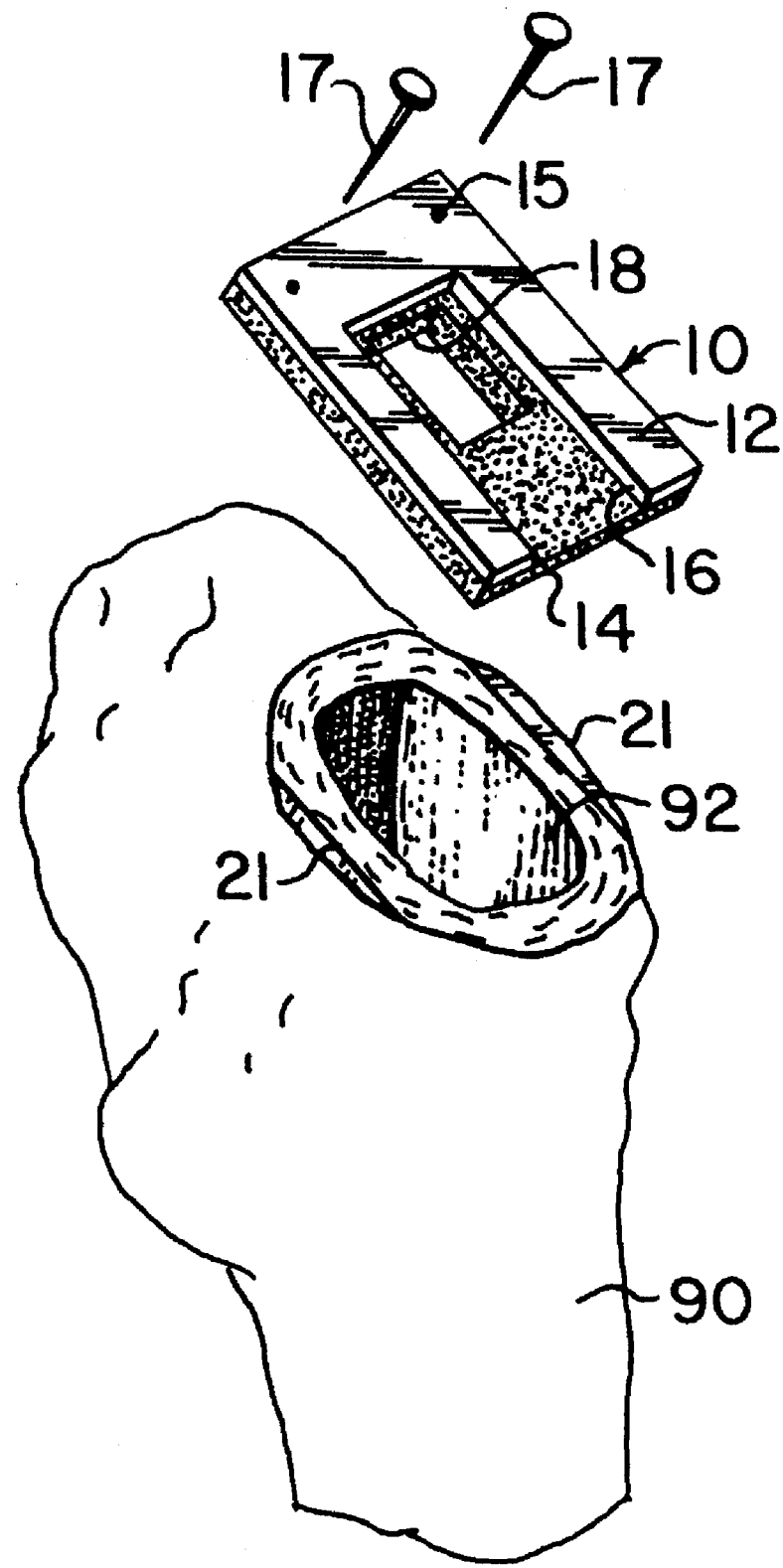
FIG. 9 is a perspective view showing another method of use of the diaphragm of FIG. 1 with a femur.

The method of the use of the embodiments illustrated in FIGS. 1, 2, and 3 will now be discribed with respect to FIGS. 5, 6, 7, 8 and 9. For purposes of illustration, use of only the embodiment of FIG. 1 will be described. However, the embodiments of FIGS. 2 and 3 may be used in substantially the same fashion, as will be obvious to one skilled in the art. FIGS. 5–9 show use of this invention with a femur 90 having a previously formed cavity 92 in the medullary canal, and femoral component 94. Component 94 has a collar 79 and head 77 and outer anterior 89, posterior 91, medial 95 and lateral 97 surfaces. First, cavity 92 is filled with cement 27 in a conventional manner. Utilizing one hand, the surgeon places diaphragm 10 over the opening in the cavity 92 at the proximal end of femur 90. Diaphragm 10 is positioned so that hole 18 is properly oriented to provide the component with the desired anteversion. Preferably a rectangular hole 18 is utilized which has the same general configuration as component 94. If desired, nail holes 15 (FIG. 9) can be provided in diaphragm 10 to allow nails 17 to be used to secure diaphragm 10 to the proximal end of the femur in the desired angular and lateral orientations during the insertion process. In an alternative embodiment, as shown in FIG. 9, the bone on the proximal end of femur 90 can be cut to form ridges 21 to assist the surgeon in properly orienting diaphragm 10 and retaining it in the desired angular and lateral orientations with respect to the femur. Preferably, the open end of slot 16 faces the medial surface 95 of femur 90, while the closed end faces lateral surface 97 of femur 90. However, other orientations of diaphragm 10 are possible. The tip 87 of component 94 is inserted into hole 18 by applying a longitudinal force to the head 77 of component 94 to push the stem thereof all the way through hole 18 until the femoral collar 79 nearly or completely rests in contact with layer 12. Cement 27 is allowed to flow out of cavity 92 only around the edges of diaphragm 10. Layer 14 is then severed within slot 16 on the side facing medial surface 95 using a knife 29 or the like. The cut extends from an edge of diaphragm 10 to hole 18. Layer 14 is then parted to allow diaphragm 10 to be removed laterally in the direction of lateral surface 97 as shown. Thereafter, component 94 is pressed downwardly into its final position in which the collar rests on the proximal end of the femur.

Figure 4:
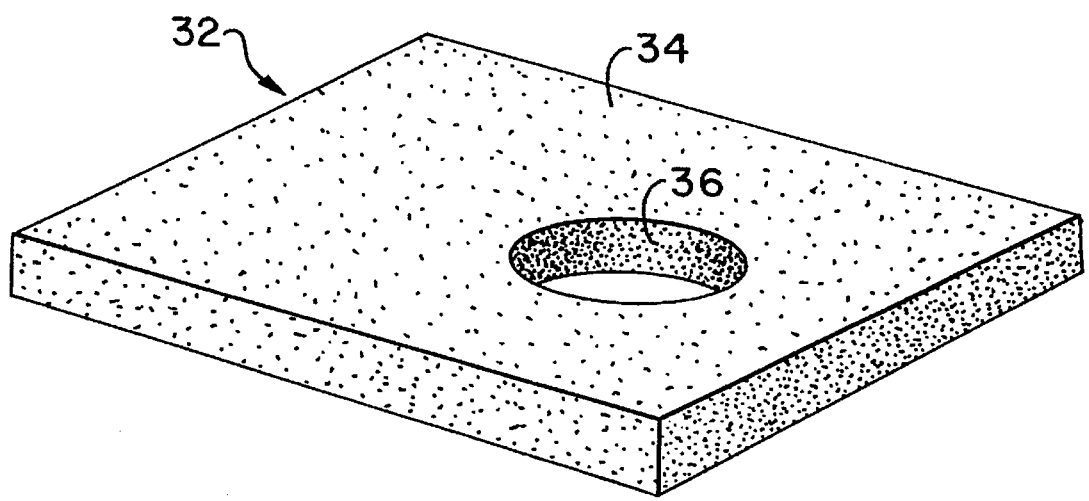
FIG. 4 is a perspective view of a third embodiment of the diaphragm of the present invention.
Figure 6:
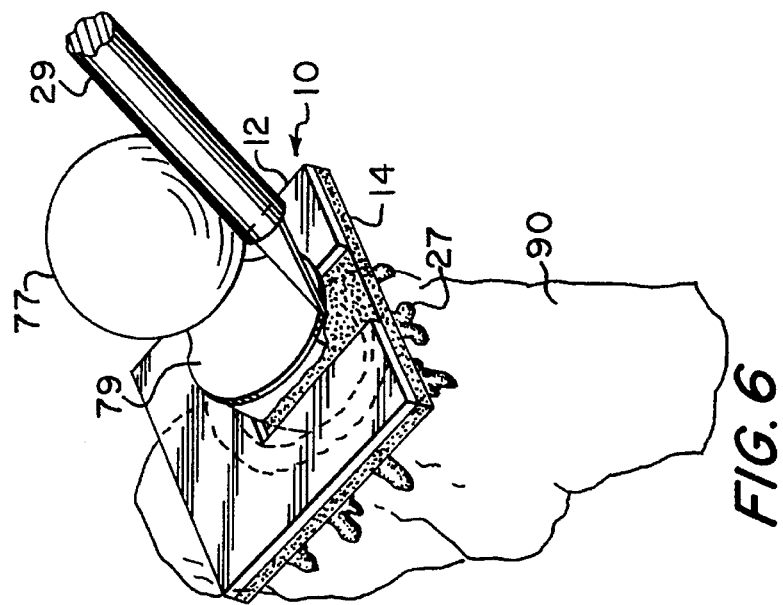
FIGS. 5–8 are perspective views showing use of the diaphragm of FIG. 1 with a femur.

Another embodiment of the present invention will now be described with reference to FIG. 4. Diaphragm 32 of FIG. 4 is a somewhat rigid layer 34 of a resilient material having a hole 36 extending therethrough from a top surface to a bottom surface. Layer 34 is formed of the same material as layers 26 and 14, except that layer 34 is provided with a somewhat greater thickness and rigidity than layers 26 and 14 so that diaphragm 32 provides the desired structural strength and rigidity to inhibit the flow of cement out of the femoral cavity. In use, a component is inserted through hole 36 with hole 36 being in snug, sealing relation with the outer surfaces thereof. The surgeon holds diaphragm 32 against the proximal end of the femur during insertion of the component. For removal of diaphragm 32, a slit is cut from hole 36 to one edge thereof to allow diaphragm 32 to be slid laterally free of the prosthesis.

Figure 10:
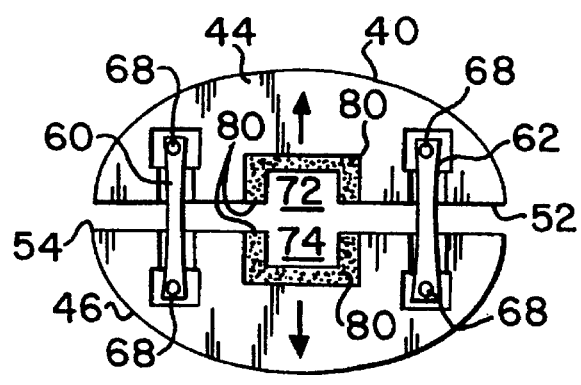
FIG. 10 is a top plan view showing one component of a fourth embodiment of the present invention.
Figure 11:
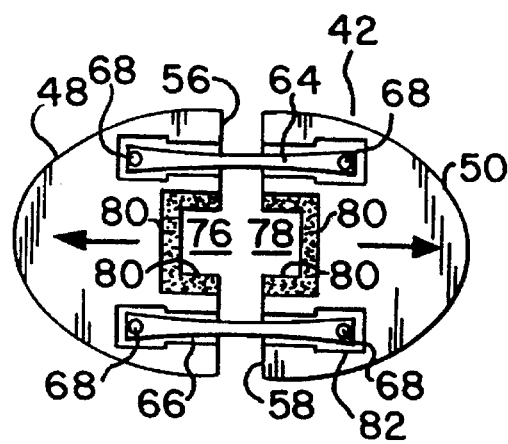
FIG. 11 is a top plan view showing a second component of a fourth embodiment of the present invention.

A further embodiment of this invention will now be described with reference to FIGS. 10 and 11. This embodiment comprises two segmented discs 40 and 42, one stacked upon the other. Discs 40 and 42 can be arranged so that disc 40 is on top or disc 42 is on top. Each disc 40 and 42 comprises a pair of segments 44 and 46, and 48 and 50, respectively. Edges 52 and 54 of respective segments 44 and 46 are disposed in abutting relation, as are edges 56 and 58 of respective segments 48 and 50. Edge 52 of segment 44 abuts and is parallel to edge 54 of segment 46. Similarly, edge 56 of segment 48 abuts and is parallel to edge 58 of segment 50. Edges 56 and 58 typically are aligned generally orthogonally to edges 52 and 54. Segments 44 and 46 are joined by elastic retainers 60 and 62. Retainers 60 and 62 bias edges 52 and 54 together. Similarly, elastic retainers 64 and 66 join segments 48 and 50 and bias together edges 56 and 58. Retainers 60, 62, 64 and 66 typically are identical. These retainers can comprise either an elastic material, or a spring which provides the necessary biasing function. In any event, retainers 60, 62, 64 and 66 are joined to their respective segments by a peg 68 to which they are attached at each end. Retainers 60, 62, and 64, 66 allow respective segments 44, 46 and 48, 50 to separate to accomodate a component as it passes between the segments, as will be described.

Figure 12:
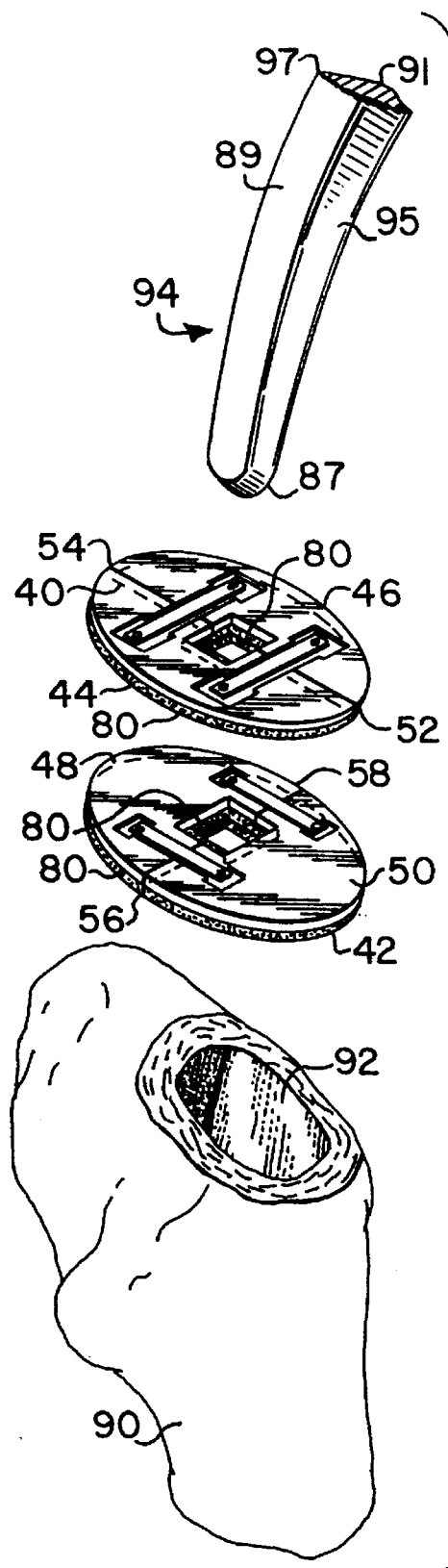
FIG. 12 is a perspective view showing use of the embodiments of FIGS. 10 and 11 with a femur.

Edges 52 and 54 include respective cutouts 72 and 74, which join to form a hole while edges 56 and 58 include respective cutouts 76 and 78 which joint to form another hole. Cutouts 72 and 74 are sufficiently wide in a dimension running generally parallel to edges 52 and 54 to accommodate the thickness of a femoral component at its widest point in one dimension. This one dimension is either the dimension from the posterior surface to the anterior surface of the component or the dimension from the medial to the lateral surface of the component. Similarly, cutouts 76 and 78 are sufficiently wide in a dimension generally parallel to edges 56 and 58 to accommodate the thickness of a femoral component at its widest point in a second dimension generally orthogonal to the one dimension accommodated by cutouts 72 and 74. This second dimension is the other of the posterior-anterior or medial-lateral dimensions. Disposed within each of cutouts 72, 74, 76 and 78 is a gasket or seal 80 which extends around the entire inner surface of its respective cutout. Seal 80 may be formed of either an elastomeric or a foam material. Examples of acceptable material include those used to form layer Seal 80 provides the desired seal along the surfaces of the femoral component as it is inserted into cutouts 72, 74, 76 and 78. Seal 80 may either be disposed on the inner surface of cutouts 72, 74, 76 and 78 or it may be formed as a separate layer disposed below segments 44, 46, 48 and 50, as shown in FIG. 12. In the latter instance, portions of seal 80 extend into cutouts 73, 74, 76 and 78, as shown, to provide the desired seal. Retainers 60, 62, 64 and 66 urge seals 80 into sealing engagement with the anterior, posterior, lateral and medial surfaces of the femoral component during insertion to prevent either cement or air from passing through cutouts 72, 74, 76 and 78.

To permit stacking of discs 40 and 42 one upon the other, accommodation must be made for retainers 60, 62, 64 and 66 and their associated pegs 68. The retainers and associated pegs on the lowermost disc 40 or 42 may be recessed into the surface thereof, or recesses may be formed on the bottom surface of the top disc to accommodate these elements and their movement with the expansion of the segments apart from one another, as will be described. For purposes of illustration, a recess 82 is shown formed on the upper surface of disc 42 to accommodate each of retainers 64 and 66 and their associated pegs 68, so that as segments 48 and 50 move with respect to one another, such movement is not impeded by friction between retainers 64 and 66 and their associated pegs 68, and the lower surface of disc 40. Discs 40 and 42 are each formed of a relatively rigid material, such as the material which forms layer 12 of FIG. 1.

Use of the embodiment of FIGS. 10 and 11 will now be described with respect to FIG. 12. First the cavity is filled with cement in a conventional manner. Disc 42 is placed over the opening of the cavity 92 formed in the medullary canal at the proximal end of the femur 90. Edges 56 and 58 are aligned so that the femoral component has the desired angular orientation or anterversion with respect to the femur. This alignment is determined by cutouts 76 and 78 which are designed to accommodate one of the two medial-lateral or posterior-anterior dimensions of the component at its widest point in a direction parallel to edges 56 and 58. Retainers 64 and 66 as well as pegs 68 are disposed in recess 82. Thereafter, disc 40 is placed on top of disc 42. Edges 52 and 54 are aligned generally orthogonally with respect to edges 56 and 58. As discussed, the dimension of cutouts 72 and 74 in a direction generally parallel to edges 52 and 54 corresponds to the other of the medial-lateral and posterior-anterior dimensions at their widest point. Discs 40 and 42 are held in place with one hand, while a surgeon inserts the tip of the femoral component 94 through the hole in disc 40 formed by mating cutouts 72 and 74 and the hole in disc 42 formed by mating cutouts 76 and 78. The seals 80 in each of the cutouts 72, 74, 76 and 78 provide a seal around the medial, lateral, anterior and posterior surfaces of the component 94 as it passes through each of the holes. As thicker portions of the femoral component pass through the holes, segments 44 and 46 expand in a direction generally normal to edges 52 and 54 against the bias of retainers 66 to accommodate the larger dimension of the component. Similarly, as the thicker portion of the component in an orthogonal direction passes through disc 42, segments 48 and 50 separate from one another at edges 56 and 58 against the bias provided by retainers 64 and 66. In this way retainers 60 and 62 and 64 and 66, maintain a seal is maintained around the perimeter of the component at all times as it passes through discs 40 and 42, yet the change in dimension of the component is accommodated.

Once the component has been inserted so that the collar (not shown) rests on disc 40, further insertion is stopped until removal of discs 40 and 42. Disc 40 is removed by either severing or removing retainers 60 and 62 so that segments 44 and 46 can be slid laterally away from the component and removed. Once disc 40 is removed, disc 42 is removed in the same way by severing or removing retainers 64 and 66 and sliding segments 48 and 50 away from one another and away from the component laterally. Thereafter, the component may be inserted the remaining distance until the collar rests snugly on the proximal surface of the femur.

In each of the foregoing embodiments, and particularly with respect to the embodiments of FIGS. 1, 7 and 8, accurate placement of the diaphragm on the proximal end of the femur allows for centering of the component in the cavity. In addition, in each of the embodiments, but particularly in the embodiments of FIGS. 1, 7 and 8, the hole provided for the component can be configured so that the component can be accepted only with a particular orientation with respect to the diaphragm. In this way, accurate orientation of the diaphragm also allows the surgeon to control the anteversion of the component. Typically, once the component is inserted into the cavity sufficiently far that the collar rests on the diaphragm, the cement will resist any further movement which may occur during removal of the diaphragm, so that anteversion and centering will not be disturbed. Moreover, in each of the foregoing embodiments, the cement is pressurized by the diaphragm during insertion of the component and thus the diaphragm assists in the distribution of the cement into the trabecular bone and permits elimination of a prior pressurization step.

The diaphragm of this invention minimizes interfacial porosity by providing a generally tight seal along the posterior, anterior, medial and lateral surfaces of the component. As a result, the amount of air drawn into the cement is minimized as the component is inserted, if not eliminated entirely. In addition, the flow patterns of the cement are altered during the insertion process, so that the cement is prevented from flowing out of the cavity, and is urged into continual contact with the metal surface of the prosthesis and no cement can escape from the cavity along the prosthesis surface. The only escape of cement that is permitted is spaced from the surface of the prosthesis at the edge of the diaphragm. Consequently, the formation of pores in the cement at the cement-metal interface is reduced, if not eliminated entirely. In pores which do form, many burst before they can be pulled down along the interface, and therefore they do not affect the interfacial porosity. As a consequence of the decrease in the interfacial porosity, the mechanical integrity of a cement mantle is improved, and thus the prospects for long term success of the prosthesis are significantly enhanced.

In view of the above description, it is likely that modifications and improvements will occur to those skilled in the art which are within the scope of this invention. The above description is intended to be exemplary only, the scope of the invention being defined by the following claims and their equivalents.

What is claimed is:

1. A combination comprising:

a femoral component adapted to be inserted into an opening of a cement-filled cavity at a proximal end of a femur, and including a stem, a neck and a collar disposed between said stem and said neck, said stem having outer medial, lateral, anterior and posterior surfaces and having a cross-sectional dimension as defined by said medial, lateral, anterior and posterior surfaces;

a covering means for covering the opening of the cement-filled cavity at the proximal end of the femur for resisting flow of cement out of the cavity during insertion of said stem of said femoral component, said covering means including a hole having a resilient seal around its perimeter which provides continuous sealing engagement between the covering means and said outer medial, lateral, anterior and posterior surfaces of said stem of said femoral component during insertion of said stem of said femoral component into the cavity, said hole having a cross-sectional dimension no greater than a minimum cross-sectional dimension of said stem of said femoral component.

2. The device as recited in claim 1 wherein said covering means comprises two layers, a first layer and a second layer, said second layer being formed of a resilient material, said first layer having a rigidity greater than a rigidity of said second layer, said second layer having said hole formed therein.

3. The device as recited in claim 2 further comprising a third layer, said third layer having a rigidity greater than the rigidity of said second layer, said second layer being disposed between said first and third layers.

4. A device as recited in claim 2 wherein said first layer comprises an elongated slot extending from one edge of said second layer and surrounding the hole in said second layer.

5. The device as recited in claim 2 wherein said second layer is formed of a material less dense than said first layer.

6. The device as recited in claim 2 wherein said second layer is formed of a flexible material having high tear resistance.

7. The device as recited in claim 1 wherein said covering means comprises an expandable disc.

8. The device as recited in claim 7 wherein said covering means comprises a first expandable disc and a second expandable disc, said first and said second discs being stacked one on top of another, said first disc expanding in a direction generally orthogonal to a direction of expansion of the second disc.

9. A device for guiding a femoral component into an opening of a cavity at a proximal end of a femur, the femoral component having outer medial, lateral, anterior and posterior surfaces and having a stem with a cross-sectional dimension as defined by its medial, lateral, anterior and posterior surfaces, said device comprising means for covering the opening of the cavity at the proximal end of a femur for resisting a flow of cement out of the cavity during insertion of the femoral component, said covering means including a hole having a resilient seal around its perimeter for providing continuous sealing engagement between said covering means and outer medial, lateral, anterior and posterior surfaces of the stem of the femoral component during insertion of the femoral component into the cavity, said covering means comprising a first expandable disc and a second expandable disc, said first and second discs being stacked one on top of another, said first disc expanding in a direction generally orthogonal to a direction of expansion of the second disc, said hole dimensioned to have a cross-sectional dimension no greater than a minimum cross-sectional dimension of the stem.

10. A device as recited in claim 9 wherein said first disc comprises:

a first segment, said first segment being elongated in a first direction, said first segment having a first edge extending in said first direction with a first cutout having a dimension in said first direction;

a second segment having a direction of elongation in said first direction and having a second edge extending in said first direction, said second edge being disposed in abutting relation with said first edge of said first segment, said second edge having a second cutout having a dimension in said direction of elongation substantially identical to said dimension of said first cutout, said first and second cutouts being disposed directly opposite one another to form the hole;

said seal being disposed about a perimeter of said first cutout and said second cutout; and means for biasing said first edge toward said second edge and for permitting said first edge to be urged away from said second edge upon application of force thereto.

11. The device as recited in claim 10 wherein said second disc comprises:

third and fourth segments, said third and fourth segments being disposed directly below said first and second segments, said third and fourth segments having respective third and fourth edges extending in a second direction generally orthogonal to said direction of elongation of said first and second segments, said third edge of said third segment being in abutting relation with said fourth edge on said fourth segment, said third and fourth edges each having respective third and fourth cutouts confronting one another, said third and fourth cutouts having said seal disposed about a perimeter thereof; and means for biasing said third edge toward said fourth edge and for allowing said third edge to be urged away from said fourth edge upon application of force thereto.

12. The device as recited in claim 11 wherein each of said first, second, third and fourth segments is formed of a generally rigid material.

13. The device as recited in claim 11 wherein each of said biasing means comprises elastic means.

14. The device as recited in claim 11 wherein each of said biasing means comprises a compression spring.

15. A combination comprising:

a femoral component including a stem, a neck and a collar disposed between said stem and said neck, said stem having outer medial, lateral, anterior and posterior surfaces, said stem of said femoral component being adapted to be inserted into a cement-filled cavity formed in a proximal end of a femur;

means for covering an opening of the cement filled cavity at a proximal end of the cavity, said covering means resisting a flow of cement out of the cavity during insertion of said stem of said femoral component;

an opening in said covering means through which the medial, lateral, anterior and posterior outer surfaces of said stem of said component are inserted; and sealing means disposed around said opening in said covering means and providing a continuous seal between said covering means and said outer medial, lateral, anterior and posterior surfaces of said stem of said femoral component for minimizing an amount of air drawn into the cement around the medial, lateral, anterior and posterior surfaces of said stem of said femoral component as said stem of said femoral component is inserted into the cement-filled cavity through said opening in said covering means.

16. The apparatus as recited in claim 15 wherein the stem of the femoral component has a cross-sectional dimension as defined by the distance between the anterior and posterior surfaces and the distance between the medial and lateral surfaces and wherein the opening has a cross-sectional size no greater than a smallest cross-sectional dimension of the stem of the femoral component.

17. The apparatus as recited in claim 15 wherein said sealing means is formed of a resilient material.

18. The apparatus as recited in claim 15 wherein said covering means comprises at least two layers, a first layer and a second layer, said first layer having a rigidity greater than said second layer, said second layer having the opening formed therein and including said sealing means.

* * * * *